United States Patent [19]
Kang et al.

[11] Patent Number: 5,230,220
[45] Date of Patent: Jul. 27, 1993

[54] STERILIZING/DEODORIZING APPARATUS FOR USE IN A REFRIGERATOR

[75] Inventors: Sung C. Kang, Suweon; Kyung M. Kim, Kweonseon, both of Rep. of Korea

[73] Assignee: Samsung Electronics Co., Ltd., Suweon, Rep. of Korea

[21] Appl. No.: 881,495

[22] Filed: May 11, 1992

[30] Foreign Application Priority Data

May 23, 1991 [KR] Rep. of Korea ............... 91-7348[U]
May 31, 1991 [KR] Rep. of Korea ............... 91-9074

[51] Int. Cl.$^5$ .......................... F25D 23/00; A61L 9/20
[52] U.S. Cl. .................................. 62/78; 62/264; 422/121
[58] Field of Search ............... 62/78, 264; 454/156; 422/5, 30, 24, 98, 121; 73/23.34, 31.02; 340/627, 632; 250/436

[56] References Cited

U.S. PATENT DOCUMENTS

| | | | |
|---|---|---|---|
| 2,288,587 | 6/1942 | Kalischer | 62/264 X |
| 4,535,247 | 8/1985 | Kurtz | 250/436 |
| 4,955,208 | 9/1990 | Kawashima et al. | 62/264 |
| 5,015,442 | 5/1991 | Hirai | 422/121 |
| 5,078,971 | 1/1992 | Matada et al. | 62/264 X |

FOREIGN PATENT DOCUMENTS

| | | | |
|---|---|---|---|
| 0291089 | 11/1989 | Japan | 62/78 |
| 0126085 | 5/1990 | Japan | 62/78 |

Primary Examiner—Harry B. Tanner
Attorney, Agent, or Firm—Burns, Doane, Swecker & Mathis

[57] ABSTRACT

A sterilizing/deodorizing apparatus for a refrigerator comprises an air intake section for introducing air thereinto, a sterilizing/deodorizing section including a discharge lamp to remove floating bacteria, odors, and the like contained in the air which passes through the intake section, a discharge section for discharging purified air. The apparatus is operated automatically by a temperature sensor or by an odor detector.

15 Claims, 6 Drawing Sheets

STERILIZING/DEODORIZING APPARATUS FOR USE IN A REFRIGERATOR

BACKGROUND OF THE INVENTION

The present invention relates to a sterilizing/deodorizing apparatus for use in a refrigerator which both sterilizes floating bacteria, which would otherwise deteriorate the freshness of stored foodstuffs, and eliminates unpleasant odors therein.

1. Prior Art

Generally, a refrigerator includes a deodorizing apparatus, with a high voltage generator mounted therein, which removes the odors. For example, the conventional deodorizing apparatus depicted in FIG. 1 is provided with a motor 12' and a high voltage generator 8' properly installed therein, an intake section 10' for introducing room air therein during the operation of the motor 12', and a deodorizing section 20 including an ozone generating electrode 9' mounted near the intake section 10'. The application of high voltage from the high voltage generator 8' to the ozone generating electrode 9' causes ozone to be generated, which removes the odors in an oxidization/deoxidization manner from the incoming air. Also provided are a residual ozone removing section 30' having an ozone removing catalyst portion for converting into Oxygen the residual non-oxidized ozone which was non-reacted at the deodorizing portion 20', and a discharging portion 40' for blowing air passing through the residual ozone removing section 30' outward.

Because this deodorizing apparatus provides only an odor removing function, a disadvantage is that it does not hinder the growth of the floating bacteria nor does it sterilize them. It also can not be expected to retard or prevent the deterioration of the freshness of stored foodstuffs.

Furthermore, when the deodorizing apparatus is used for an extended period of time, a problem develops when the ozone generating electrode has impurities such as dust particles attached to the surface thereof, so that the amount of ozone generated decreases which affects the removal of the odors from the refrigerator. The refrigerator operation control is randomly activated by applying the power source at predetermined intervals, thereby failing to accomplish an effective deodorizing function due to the extended use and the consequential unnecessary power consumption.

A main object of the invention is to provide a sterilizing/deodorizing apparatus for a refrigerator for automatically sterilizing floating bacteria and removing odors to maintain the uniform freshness of stored foodstuffs.

SUMMARY OF THE INVENTION

According to the present invention, a sterilizing/deodorizing apparatus for a refrigerator comprises an air intake section for introducing room air thereinto while in operation; a sterilizing/deodorizing section including means for sterilizing floating bacteria and removing unpleasant odors, etc. contained in the air passing through the intake section; a residual ozone removing section having an ozone removing catalyst for converting non-oxidized ozone from the sterilizing/deodorizing section into Oxygen; a discharging section having a fan attachment driven by a motor for blowing purified air through the residual ozone removing section outward; and an automatic control section for controlling the operation of the sterilizing/deodorizing section and the motor.

Herein, the automatic control section is provided with an odor sensor and its periphery circuit. The provision of the odor sensor is devised from the view-point of generating floating bacteria along with odors.

BRIEF DESCRIPTION OF THE DRAWINGS

The present invention will now be further described with reference to the accompanying drawings, in which.

DETAILED DESCRIPTION OF PREFERRED EMBODIMENTS

Figure 1:
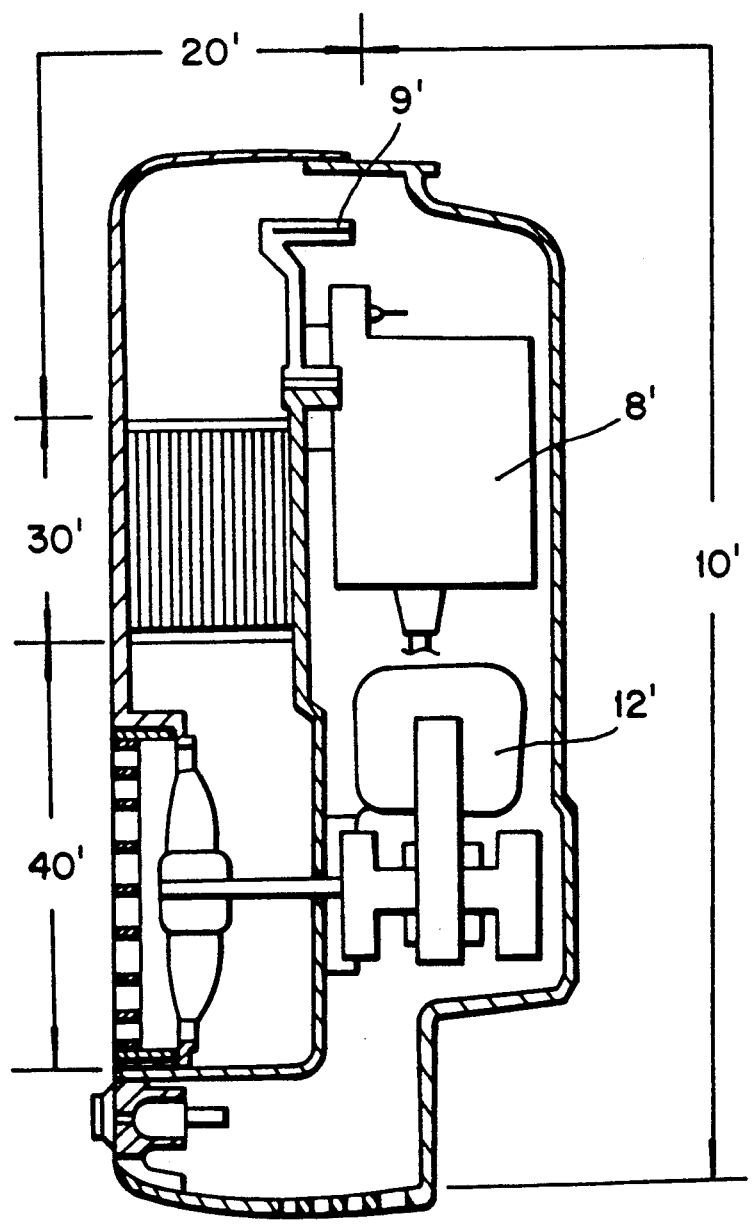
FIG. 1 is a cross-sectional view showing a deodorizing apparatus of a refrigerator in accordance with prior art.
Figure 2:
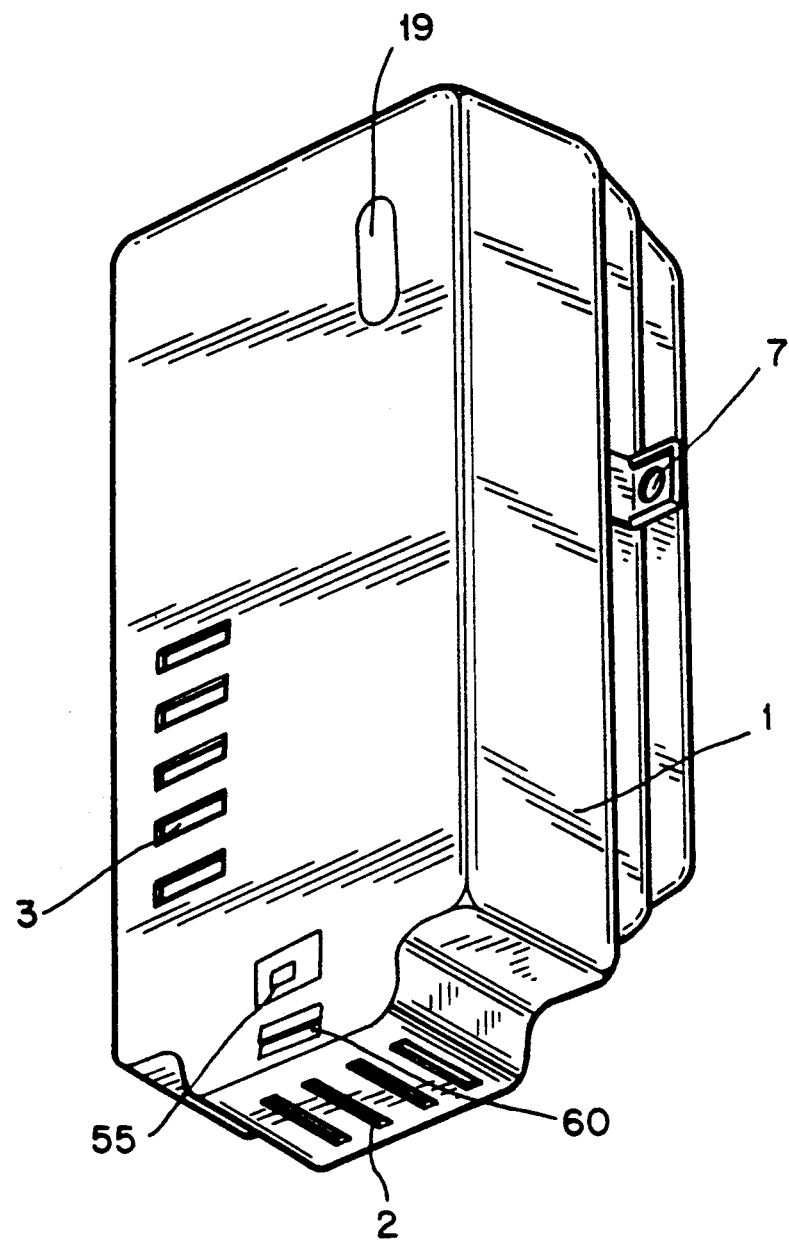
FIG. 2 is a perspective view showing a sterilizing/deodorizing apparatus for a refrigerator in accordance with the present invention.

Referring to FIGS. 2-5, a housing 1 constituting the outer wall of a sterilizing/deodorizing apparatus for a refrigerator, in the bottom of which an inlet 2 is configured to intake chamber air therein and on the front of which an outlet 3 is placed through which purified air is discharged. A separating member 4 is located in the inner portion of the housing 1 to divide the inner portion into a left chamber portion 5 and a right chamber portion 6. A fixing member 7 is integrally formed on both side edges of the housing 1 to allow the apparatus to be properly removed from and/or positioned in the refrigerator.

The inner right chamber portion 6 includes a motor 12 installed near the lower portion by means of a mounting member 11. The motor 12 is provided with a fan blade 41 shafted thereto, which is positioned in the left chamber portion 5. The lower portion of the right chamber portion 6 forms an air intake section 10 along with the intake portion 2 placed at the lowest part of the housing 1.

A sterilizing/deodorizing section 20 is placed in the upper portion of the right chamber portion 6 in order to sterilize and deodorize floating bacteria and odors introduced from the air intake section 10. The sterilizing/deodorizing section 20 comprises a discharge lamp 21 fixed by means of a supporting member 22 to its rear wall, which radiates ultraviolet rays consisting of two wave lengths of 254 nm and 185 nm, so that each of the wave lengths serves to sterilize floating bacteria and generate ozone for removing odors in an oxidization/deoxidization manner.

The sterilizing/deodorizing section 20 has ultraviolet ray shielding plates 23 surrounded on the inner wall thereof except for an emanating portion 44 and the air passage portion connected with the intake section 10. The shielding plates 23 function to reflect the ultraviolet rays and prevent their leakage, so that the sterilizing-/deodorizing effect of the discharge lamp 21 is better promoted. A printed circuit board 26 is fixed to the shielding plate 23 adjacent to the discharge lamp 21. The sterilizing/deodorizing section 20 extends from the passage portion at the entrance end of the discharge lamp 21 to a residual ozone removing section 30. The length may be less than 150 mm and is ideally 150 mm for facilitating the sterilization/deodorization of the intake air.

The residual ozone removing section 30 is positioned adjacent to approximately the middle portion of the discharge lamp 21 in the left chamber portion 5 without the ultraviolet rays being directly radiated thereon. Also, the residual ozone removing section 30 contains an ozone removing catalyst for converting non-oxidized residual ozone from the sterilizing/deodorizing section 20 into Oxygen. Below the residual ozone removing section 30 an air discharging section 40 is positioned.

The air discharging section 40 is provided with the fan member 41 arranged in an isolating portion 43 which is separated by means of a partition member 42.

The fan blade 41 has a shaft 13 connected through a hole 8 to the motor 12, so that during its operation the motor 12 intakes air from the intake section 10 and then discharges the purified air into the refrigerator. Around the hole 8 a sealing member 9 is attached to prevent the circulation of air between the air discharging section 40 and the air intake section 10.

The housing 1 has an indicating window 19 and an odor sensor 60 provided on the front thereof which permits the user to visually confirm the operating states of the discharge lamp 21.

On the other hand, a sterilizing/deodorizing apparatus according to the present invention is controlled in conjunction with the operations of a temperature adjustment switch 51 and a defrost timer 52 which adjust the temperature and control the defrosting phase in the refrigerator, respectively.

Figure 6:
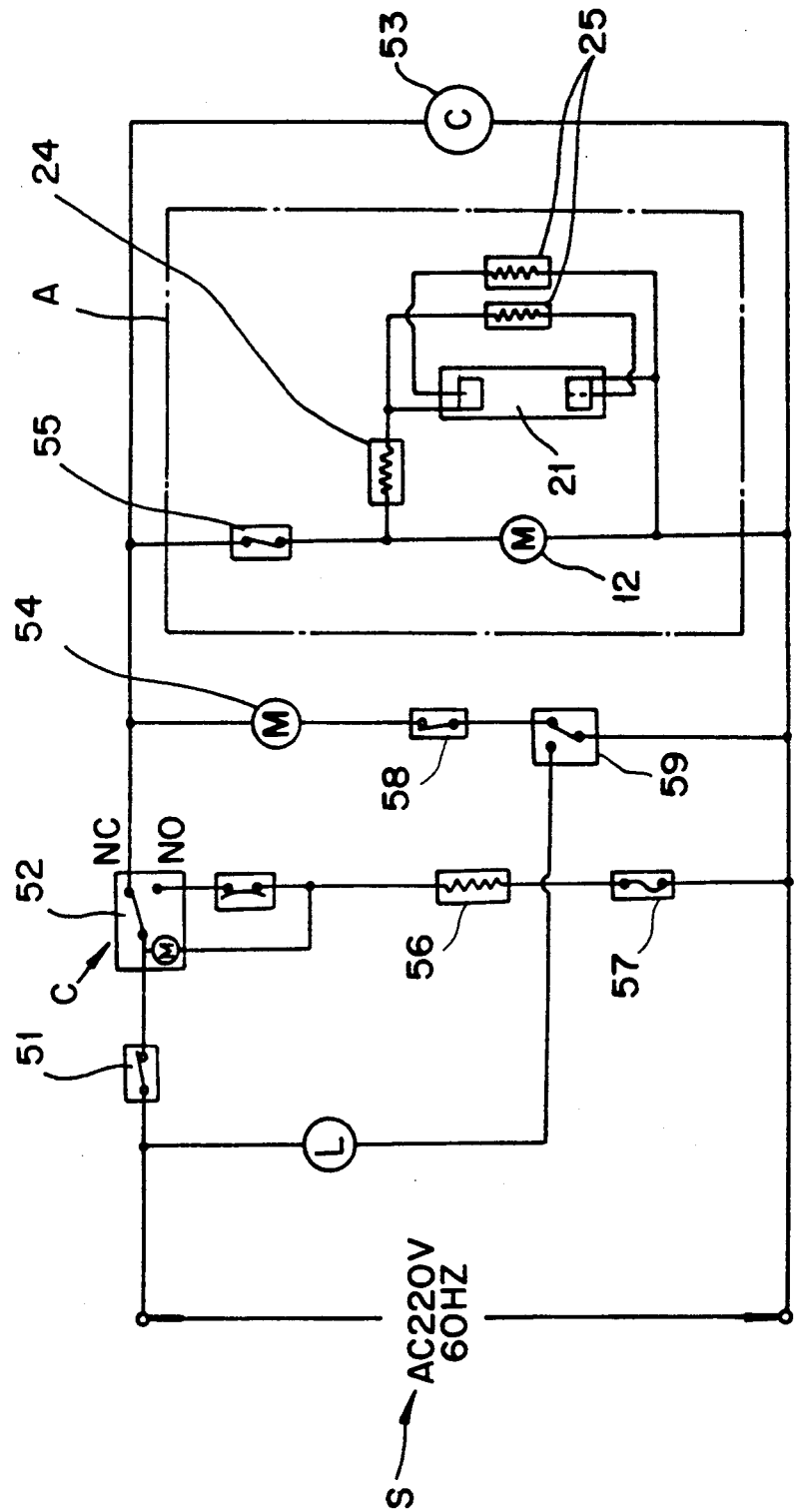
FIG. 6 depicts a circuit for controlling the operation of a sterilizing/deodorizing apparatus for a refrigerator in accordance with the present invention; and, FIG. 7 depicts another embodiment of a circuit for controlling the operation of a sterilizing/deodorizing apparatus for a refrigerator in accordance with the present invention.

Referring to FIG. 6, the refrigerator is normally operated in a manner whereby the temperature adjustment switch 51 is turned on, and the defrost timer 52 is switched to connect the fixing terminal C to the selecting terminal NC. At that time the power source S (A.C. 220 V, 60 Hz) is applied to a fan motor 54 and a compressor 53, so that the fan motor 54 circulates air in the refrigerating chambers, and the compressor 53 performs the refrigerant cycle along with an evaporator and a condenser (not shown). A lamp L is activated by a refrigerator opening/closing switch 59. When the fixing terminal C is connected to the selecting terminal NO after a predetermined amount of time, the defrost timer 52 activates a defrost heater 56 to remove frost accumulated on the evaporator. Reference nos. 57 and 58 are, respectively, a fuse for the defrost heater 56 and a switch for the fan motor 54.

Figure 3:
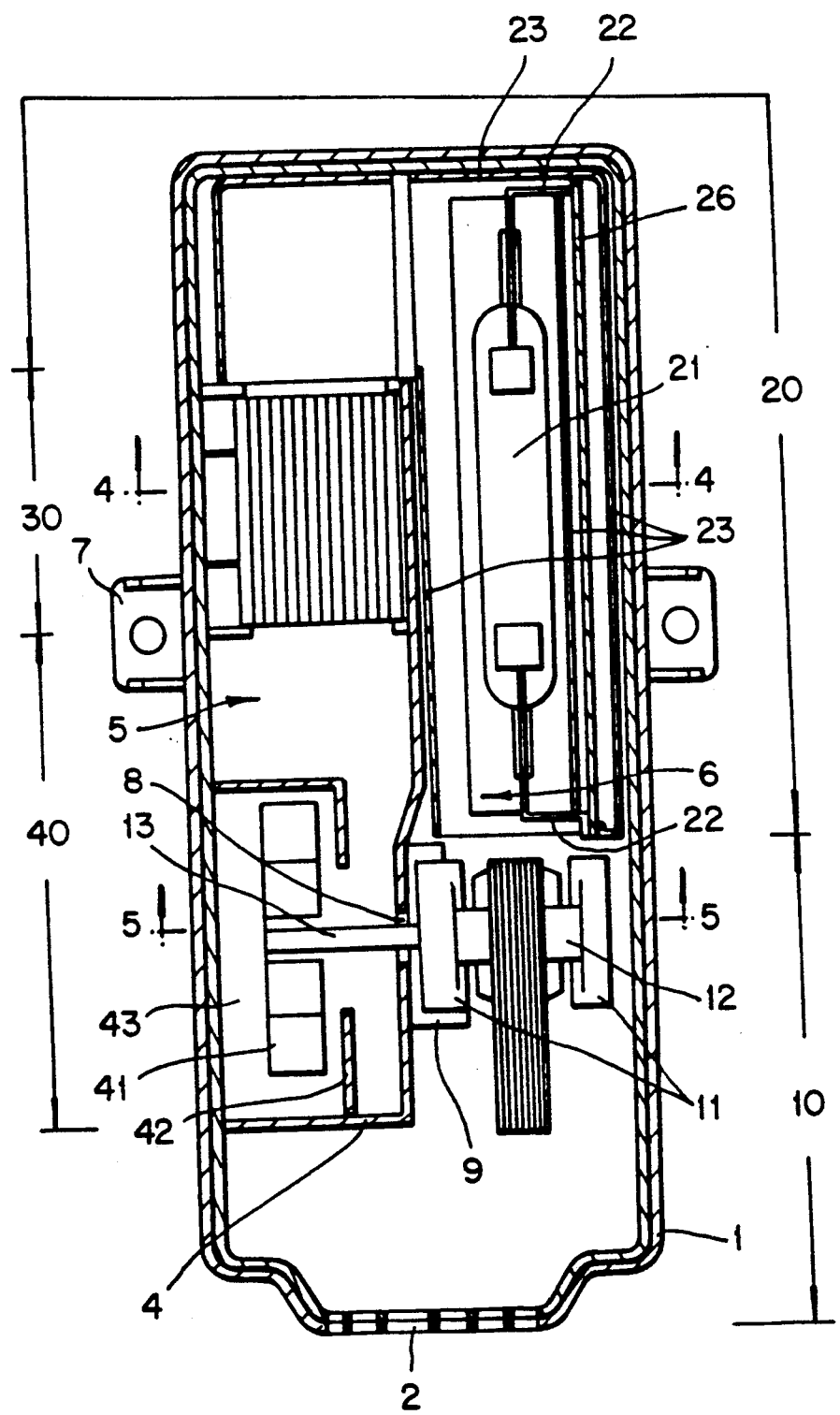
FIG. 3 is a cross-sectional view through the sterilizing/deodorizing apparatus of FIG. 2.
Figure 4:
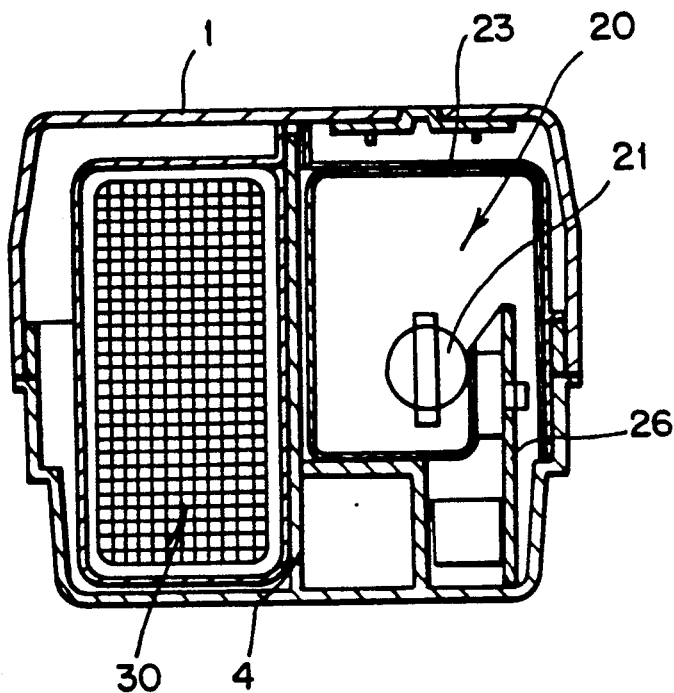
FIG. 4 is a sectional view taken along line 4—4 of FIG. 3.
Figure 5:
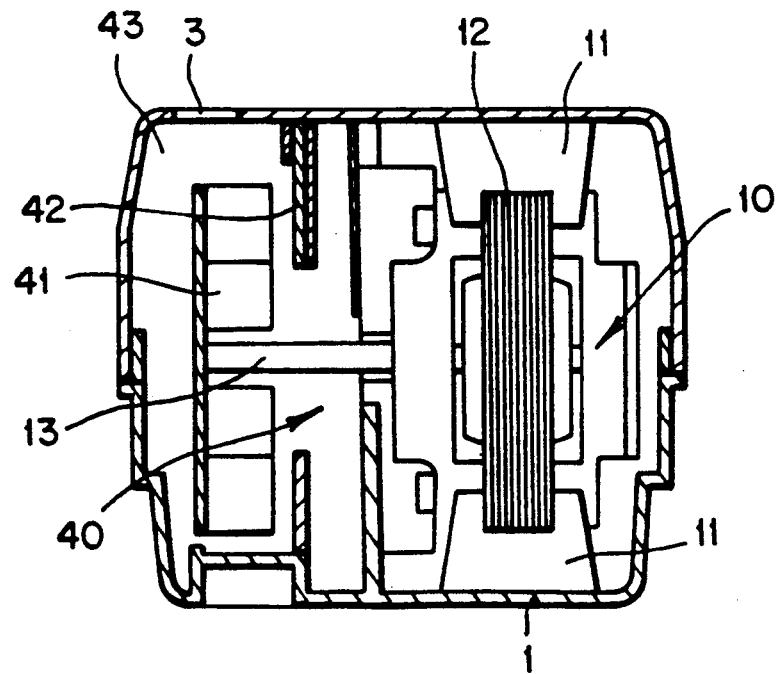
FIG. 5 is a sectional view taken along line 5—5 of FIG. 3.

Therefore, the control circuit A, which operates the sterilizing/deodorizing apparatus is provided with an operating switch 55. The operating switch 55 is connected in series to the motor 12. The motor 12 is coupled in parallel to a discharge lamp 21 through a ballast 24 which applies a predetermined voltage to the discharge lamp 21. The discharge lamp 21 is provided with two resistors 25 which are coupled in parallel to each other and in series to respective electrodes of the discharge lamp 21. Herein, the ballast 24 and the resistors 25 have a predetermined resistance value which activates the discharge lamp 21 under low temperature and/or low voltage conditions (for example, below 5° C. and 190 V). An amount of gas, for example Mercury and Argon, sealed into the discharge lamp 21 is adjusted to maintain the conditions. Also, the resistors 25, the ballast 24 and supporting members 22 (as shown in FIG. 3) are mounted on the printed circuit board 26 between shielding plates 23. The control circuit A is operated by the operating switch 55 in a manner whereby the motor 12 is driven to cause the fan blade 41 to circulate the refrigerating air through the discharge lamp 21, and the discharge lamp 21 is activated in order to sterilize floating bacteria and deodorize odors.

Figure 7:
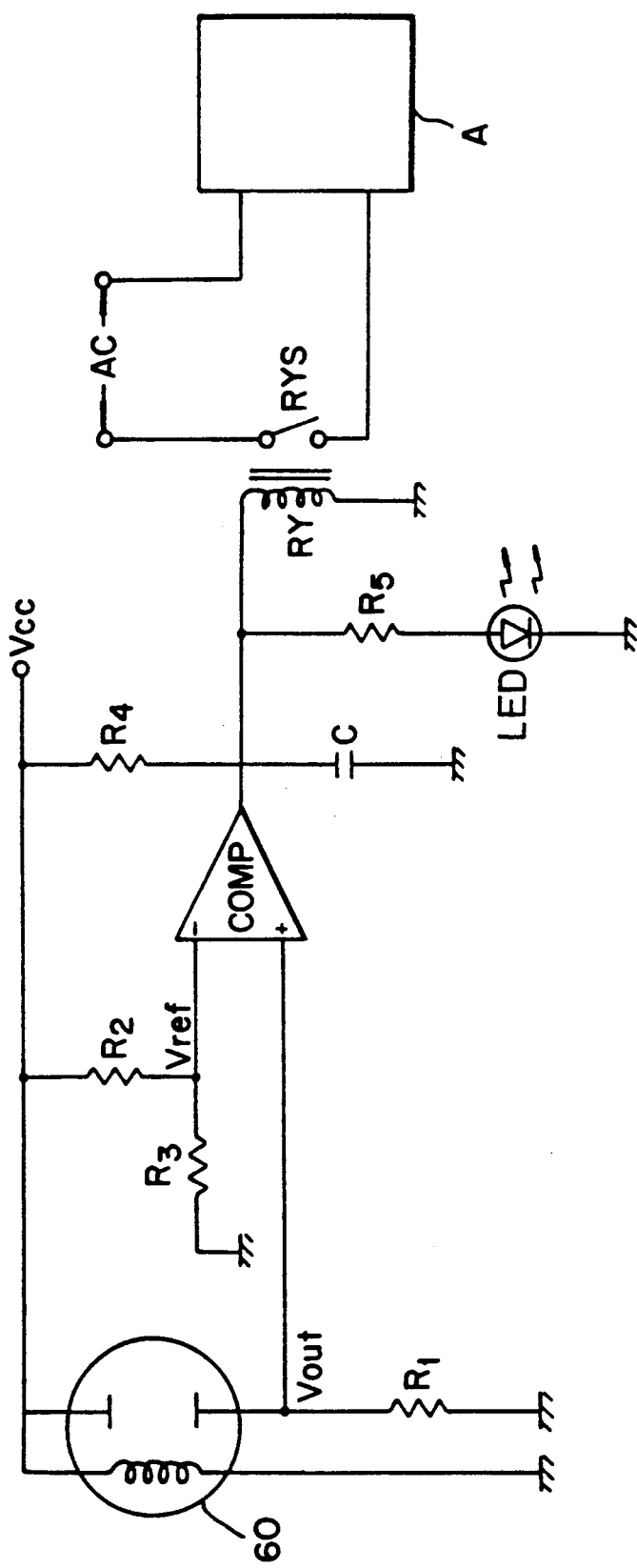

FIG. 7 is the schematic drawing of a circuit illustrating another embodiment for automatically controlling the operation of the control circuit A of the present invention. The odor sensor 60 is connected in series to a voltage source Vcc and grounded through a resistor $R_1$ at its resistance side. The resistor $R_1$ is connected at a tap Vout called the output voltage of the odor sensor 60 to the non-inverting terminal(+) of a comparator COMP. The comparator COMP is connected at the inverting terminal(−) to a tap Vref having a reference voltage which divides the voltage source Vcc into resistors $R_2$ and $R_3$. The output terminal of the comparator COMP is connected through a resistor $R_4$ and a capacitor C to a relay RY. It is also connected to a light emitting diode LED connected to a resistor $R_5$. The relay RY is provided with a relay switch RYS to coordinate with a control circuit A of FIG. 6.

Therefore, during its operation, the odor sensor 60 detects odors generated by foodstuffs stored in the refrigerator. As the amount of detected odor increases, the odor sensor 60 varies its resistance value to determine the output voltage Vout to the voltage source Vcc. The output voltage Vout is applied to the non-inverting terminal (+) of the comparator COMP. The comparator COMP compares the output voltage Vout to the reference voltage Vref of its inverting terminal (−).

When there is no odor in the refrigerator, the resistance value of the odor sensor 60 becomes very high, which causes the output voltage Vout to be lower than the reference voltage Vref going to the comparator COMP. The comparator COMP sends low level signals when the light emitting diode LED is turned off, and the switch RYS of the relay RY is opened because the coil of the relay RY is not energized. As a result, AC voltage is not applied to the control circuit A of the sterilizing/deodorizing apparatus.

On the contrary, when there are many odors in the refrigerator, the output voltage Vout becomes higher than the reference Vref because the resistance value of the odor sensor 60 becomes relatively lower. At that time, the comparator COMP sends high level signals, the light emitting diode LED is turned on, and the switch RYS is closed because the coil of the relay is energized. The source voltage AC is then applied to the control circuit of the sterilizing/deodorizing apparatus, whereby the sterilizing/deodorizing apparatus is activated to sterilize floating bacteria and eliminate odors in the refrigerator.

The sterilizing/deodorizing apparatus controlled by the FIG. 6 control mechanism is activated by turning on an operating switch 55. The control circuit A is automatically energized whenever the terminals N and NC are interconnected. Initially, the motor 12 is driven to rotate the fan blade 41, so that air in the refrigerator is forced through the air intake section 10 into the sterilizing/deodorizing section 20. The discharge lamp 21 purifies air in the refrigerator, whereby the ultraviolet ray of 185 nm generates ozone to remove odors in an oxidation/deoxidation manner, and the ultraviolet ray of 254 nm sterilizes bacteria floating in the air. Then, the intake air is forced through the residual ozone removing section 30, in which the residual nonreacted ozone at the sterilizing/deodorizing section 20 is converted into Oxygen by the catalyst contained in the residual ozone removing section. Along with the oxygen, the intake air is completely purified and then discharged through the air discharge section 40, thereby allowing foodstuffs in the refrigerator to be maintained in a fresh condition. If the FIG. 7 control mechanism is utilized, then the sterilizing/deodorizing apparatus is automatically operated by the odor sensor 60.

As can be seen from the above, the function for removing odors is added by the present invention to the prior art, functions thereby promoting its performance. Also, the automatic operation of the present invention provides the appliance with reliability of products for the benefit of the user and prevents unnecessary power consumption and prolongs the appliance's useful lifetime.

What is claimed is:

1. A sterilizing/deodorizing apparatus for a refrigerator comprising:
    an air intake for receiving air from the inside space of a refrigerator;
    a sterilizing/deodorizing section communicating with said intake for receiving air therefrom; said sterilizing/deodorizing section including means for sterilizing bacteria and deodorizing odors contained in the air;
    a residual ozone removing section communicating with said sterilizing/deodorizing section for receiving air through and having an ozone removing catalyst for converting non-oxidized ozone into oxygen;
    an outlet communicating with said ozone-removing section for discharging air back into the inside space of the refrigerator; and
    air circulating means for circulating air through said inlet, said sterilizing/deodorizing section, said residual ozone removing section, and said outlet.

2. A sterilizing/deodorizing apparatus according to claim 1 including an air discharging section defining said outlet, said air circulating means comprising a motor-driven fan disposed in said air discharging section.

3. A sterilizing deodorizing apparatus according to claim 1, wherein said means for sterilizing and deodorizing comprises a discharge lamp for generating ultraviolet rays.

4. A sterilizing/deodorizing apparatus according to claim 3, wherein said discharge lamp generates ultraviolet rays having wave lengths of 185 nm and 254 nm.

5. A sterilizing/deodorizing apparatus according to claim 3, wherein said sterilizing/deodorizing section includes ultraviolet ray shielding plates for preventing leakage of the generated ultraviolet rays.

6. A sterilizing/deodorizing apparatus according to claim 1, wherein said sterilizing/deodorizing section includes a window to allow a user to visually observe operation.

7. A sterilizing/deodorizing apparatus according to claim 1, wherein said sterilizing/deodorizing section has a length less than 150 mm.

8. A sterilizing/deodorizing apparatus according to claim 1 including control means for automatically energizing said air circulating means.

9. A sterilizing/deodorizing apparatus according to claim 8, wherein said control means includes a mechanism for flowing air within said refrigerator space, said mechanism including a temperature sensing switch and a timer, said mechanism being connected to actuate said air circulating means and said means for sterilizing bacteria and deodorizing odors when said mechanism flows cold air within said refrigerator space.

10. A sterilizing/deodorizing apparatus according to claim 8, wherein said control means includes means for detecting odors in said refrigerator space.

11. A sterilizing/deodorizing apparatus according to claim 10 including a housing in which said air intake, said sterilizing/deodorizing section, said residual ozone removing section; said outlet, and said air circulating means are housed, said odor detecting means mounted on the outside of said housing.

12. A sterilizing/deodorizing apparatus according to claim 10, wherein said odor detecting means includes means for generating a voltage output in accordance with detected odors, said control means further including comparing means for comparing the output voltage of said odor detecting means with a reference voltage, and a switching means controlled by said comparing means for applying a voltage to said means for sterilizing and deodorizing means and to said air circulating means.

13. A sterilizing/deodorizing apparatus according to claim 12, wherein said switching means comprises a relay.

14. A sterilizing/deodorizing apparatus according to claim 8, wherein said air circulating means includes a motor; said means for sterilizing and deodorizing comprising a discharge lamp for generating ultraviolet rays; said control means comprising an operating switch connected in series to said motor; said discharge lamp including electrodes; each of said electrodes connected in series to a respective resistor; said electrodes and said resistors connected in parallel to each other to said motor through a ballast.

15. A sterilizing/deodorizing apparatus according to claim 14, wherein said resistors, said ballast, and said means for sterilizing and deodorizing being assembled on a substrate; said substrate being surrounded by ultraviolet shielding plates.

* * * * *